United States Patent [19]

Tabak

[11] Patent Number: 4,654,453
[45] Date of Patent: Mar. 31, 1987

[54] PROCESS FOR CONVERTING OXYGENATES TO HYDROCARBONS

[75] Inventor: Samuel A. Tabak, Wenonah, N.J.

[73] Assignee: Mobil Oil Corporation, New York, N.Y.

[21] Appl. No.: 779,346

[22] Filed: Sep. 23, 1985

[51] Int. Cl.$^4$ .............................................. C07C 1/24
[52] U.S. Cl. .................... 585/303; 585/315; 585/322; 585/323; 585/408; 585/413; 585/469; 585/475; 585/415; 208/80
[58] Field of Search ............... 585/408, 407, 413, 415, 585/315, 322, 323, 475, 303, 469; 208/78, 80

[56] References Cited

U.S. PATENT DOCUMENTS

| | | | |
|---|---|---|---|
| 3,969,426 | 7/1976 | Owen et al. | 585/322 |
| 3,972,958 | 8/1976 | Garwood et al. | 208/10 |
| 4,025,576 | 5/1977 | Chang et al. | 585/322 |
| 4,048,250 | 9/1977 | Garwood et al. | 518/728 |
| 4,105,707 | 8/1978 | Little et al. | 585/322 |
| 4,211,885 | 7/1980 | Banks | 585/316 |
| 4,423,274 | 12/1983 | Daviduk et al. | 585/640 |
| 4,433,188 | 2/1984 | Hoelderich et al. | 585/408 |
| 4,444,988 | 4/1984 | Capsuto et al. | 585/322 |
| 4,499,314 | 2/1985 | Seddon et al. | 585/408 |
| 4,523,046 | 6/1985 | Gould et al. | 585/408 |
| 4,547,613 | 10/1985 | Garwood et al. | 585/408 |
| 4,579,999 | 4/1986 | Gould et al. | 585/322 |

OTHER PUBLICATIONS

S. A. Tabak et al, "New Synthetic Fuel Routes for Production of Gasoline and Distillate", paper presented at Synfuels: 4th Worldwide Symposium, Nov. 7-9, 1984.

Primary Examiner—Andrew H. Metz
Assistant Examiner—Anthony McFarlane
Attorney, Agent, or Firm—Alexander J. McKillop; Michael G. Gilman; L. G. Wise

[57] ABSTRACT

Aliphatic oxygenates are converted to high octane gasoline by an integrated process wherein three reaction zones are utilized. In a first reaction zone the oxygenates are directly converted to gasoline and an isobutane by-product. In a second reaction zone oxygenates are dehydrated to an intermediate product comprising $C_3$–$C_4$ olefins, which are then further reacted with the isobutane by-product in a third reaction zone to yield a gasoline alkylate. Ethylene-containing vapors may be separated from the second reaction zone and recycled to the first reaction zone for further processing.

10 Claims, 1 Drawing Figure

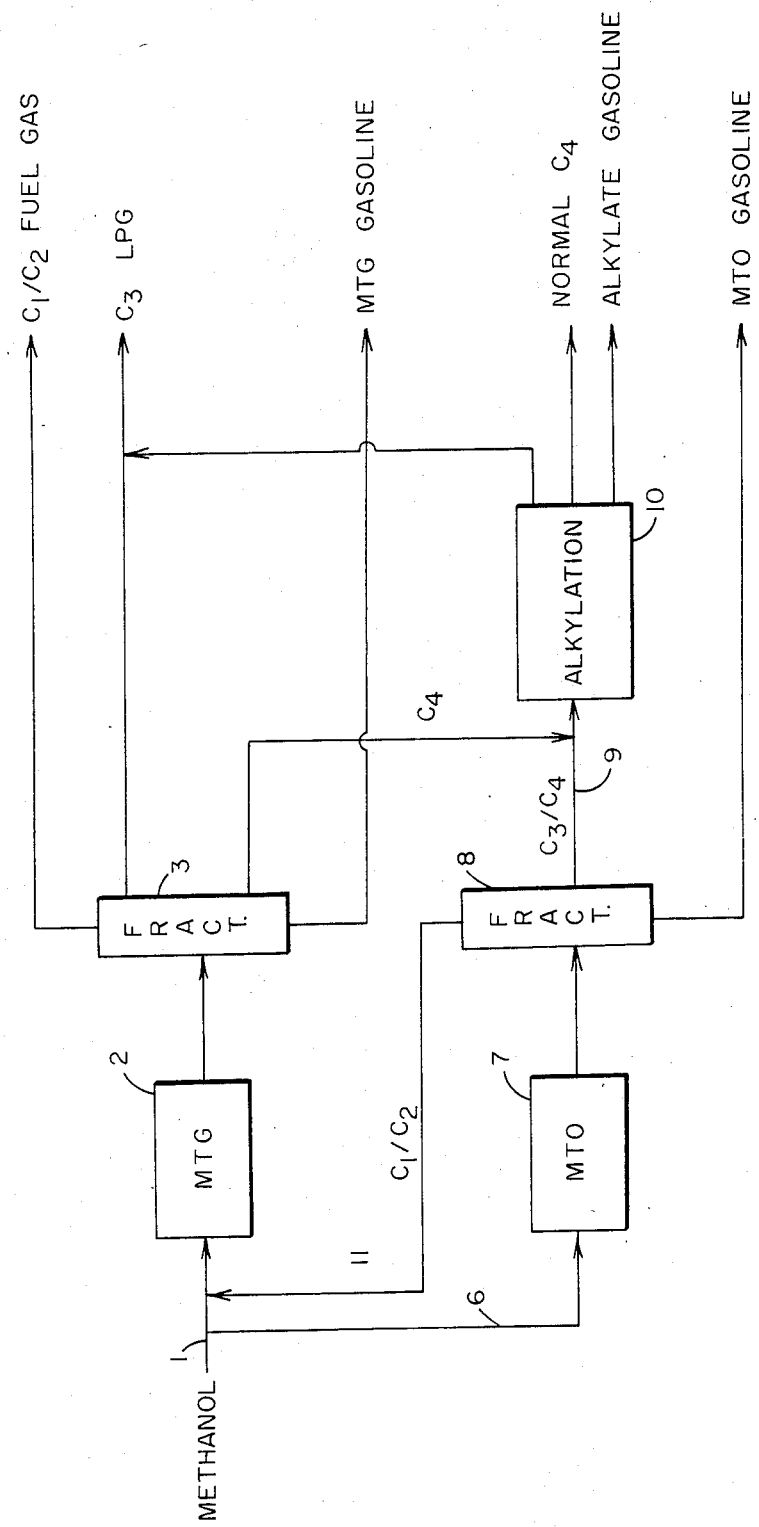

PROCESS FOR CONVERTING OXYGENATES TO HYDROCARBONS

BACKGROUND OF THE INVENTION

This invention relates to an integrated process for converting oxygenates such as methanol and dimethyl ether (DME) to liquid hydrocarbons. The oxygenate feedstock is contacted with a zeolite catalyst in a reaction zone to distillate and/or gasoline through an intermediate olefinic material.

It is also known to contact an oxygenate feedstock with a dehydration catalyst to produce lower olefins, which may be employed as starting materials for producing gasoline. The $C_3$–$C_4$ olefins are mixed with isobutane and directed to an acid alkylation reaction zone to yield a valuable alkylate gasoline.

The following patents are examples of related prior art. Their disclosures are incorporated herein by this reference to them.

U.S. Pat. No. 3,972,958 (Garwood et al) discloses a process for converting coal to high octane gasoline which includes the step of alkylating the $C_3$–$C_4$ olefins with isobutane.

U.S. Pat. No. 4,211,885 (Banks) discloses a process for producing high octane gasoline which includes the step of alkylating a butenes stream with isobutane.

The foregoing patents do not teach the concept of providing an alkylation unit with a feedstock derived from a combination of an MTG (methanol to gasoline) reactor and an MTO (methanol to olefin) reactor.

SUMMARY OF THE INVENTION

It has been discovered that improved yield of high octane gasoline may be obtained by providing a small MTO (methanol to olefin) conversion unit and an alkylation reaction unit in conjunction with a large-scale MTG (methanol to gasoline) reaction zone. In a fixed-bed MTG process relatively large amounts of isobutane are produced, eg., about 8% by weight of hydrocarbons product. In the past, it has been the practice to draw off the isobutane fraction without an immediate upgrading step.

In the present process, isobutane from the MTG process may be contacted with $C_3$–$C_4$ olefins, derived from the MTO unit, to produce gasoline in an alkylation zone. The overall yield of high octane gasoline from the MTG process is thus greatly increased.

In a further improvement, the ethylene-containing vapors are separated from the other products of the MTO process and recycled to the MTG reaction zone.

BRIEF DESCRIPTION OF THE DRAWING

The FIGURE is a process flow diagram depicting the multistage integrated system.

DESCRIPTION OF PREFERRED EMBODIMENTS

The feedstock for both the MTG and the MTO processes is lower molecular weight oxygenated organic compound(s). Examples of such compounds are aliphatic alcohols, ethers, ketones, and aldehydes. Since methanol or its ether derivative (DME) are industrial commodities available from synthesis gas or the like, these materials are utilized in the description herein as preferred starting materials. It is known in the art to partially convert oxygenates by dehydration, as in the catalytic reaction of methanol over gamma-alumina to produce DME intermediate. Typically, a mixture ($CH_3OH + CH_3$—O—$CH_3 + H_2O$) is produced by partial dehydration. This reaction takes place in both conversion of methanol to gasoline (MTG) and methanol to lower olefins (MTO).

The zeolite catalysts preferred for use in both MTO and MTG processes herein include the crystalline aluminosilicate zeolites having a silica to alumina ratio of at least 12, a constraint index of about 1 to 12 and acid cracking activity of about 1–200. Representative of the ZSM-5, ZSM-11, ZSM-12, ZSM-22, ZSM-23, ZSM-35 and ZSM-38. ZSM-5 is disclosed and claims in U.S. Pat. No. 3,702,886 and U.S. Pat. No. Re. 29,948; ZSM-11 is disclosed and claimed in U.S. Pat. No. 3,709,979. Also, see U.S. Pat. No. 3,832,449 for ZSM-12; U.S. Pat. No. 4,076,842 for ZSM-23; U.S. Pat. No. 4,016,245 for ZSM-35 and U.S. Pat. No. 4,046,839 for ZSM-38. The disclosure of these patents are incorporated herein by reference. A suitable catalyst for oxygenate conversion is HZSM-5 zeolite with alumina binder. These medium pore shape selective catalysts are sometimes known as porotectosiliciates or "pentasil" catalysts.

Other catalysts and processes suitable for converting methanol/DME to lower olefins are disclosed in U.S. Pat. No. 4,393,265 (Bonifaz), U.S. Pat. No. 4,387,263 (Vogt et al) and European Patent Application No. 0081683 (Marosi et al), and ZSM-45. In addition to the preferred aluminosilicates, the borosilicate, ferrosilicate and "silicalite" materials may be employed. ZSM-5 type catalysts are particularly advantageous because the same material may be employed for dehydration of methanol to DME, conversion to lower olefins and ethylene conversion.

Referring to the drawing 1, the process feedstock (methanol and/or DME, for instance) is directed via conduit 1 to a fixed-bed MTG catalytic reactor 2. Oxygenate feedstock is converted predominantly to gasoline range hydrocarbons in this first reactor zone, in contact with ZSM-5 type zeolite catalyst, thereby producing a minor amount of isobutane. The effluent from reactor 2 is conducted to fractionation system 3 where it is separated into a gasoline fraction, an isobutane-rich $C_4$ stream, a $C_3$ liquified petroleum gas (LPG) fraction, and an overhead stream of $C_1$–$C_2$ fuel gas.

A portion of the process feedstock (methanol and/or DME) is directed via conduit 6 to a catalytic MTO reactor 7. Effluent from reactor 7 is conducted to a fractionation system 8 where it is separated into a gasoline fraction, an ethane-rich fraction and a $C_3$–$C_4$ olefin fraction. The $C_3$–$C_4$ olefin stream from fractionator 8 is directed via conduit 9 to acid alkylation unit 10, where it is combined with the isobutane rich $C_4$ stream to alkylate the isobutane with $C_3$–$C_4$ olefins in the third reactor zone in contact with an acid catalyst.

By converting oxygenate feedstock predominantly to $C_2$–$C_5$ lower olefins in the second reactor zone 7 in contact with zeolite catalyst, separating an ethene rich stream 11 from the second reactor olefinic effluent and further converting the ethene to heavier hydrocarbons in the first reactor zone 2, a balanced multistage process is achieved.

The MTO process may be optimized to produce at least 30% $C_3$–$C_4$ olefins by employing fluid bed primary stage conditions in the temperature range of about 425° C. to 550° C., a pressure range of about 100 to 800 kPa and weight hourly space velocity range of about 0.5 to 3.0 based on ZSM-5 type catalyst (alpha=1–50) and methanol equivalent in the primary stage feedstock. Suitable equipment and operating conditions are described in U.S. patent application Ser. No. 687,045 filed 28 Dec. 1984, now U.S. Pat. No. 4,547,616, incorporated herein by reference.

The MTG process unit may be a fixed bed type, as disclosed in U.S. Pat. Nos. 3,894,107; 3,928,483; 3,931,349; 4,048,250; etc. It is known to recycle ethene in the production of aromatic gasoline from methanol over zeolites (U.S. Pat. No. 3,998,899, Daviduk). In a fluidized bed plant for converting methanol to lower olefins and gasoline, recycle of ethylene at a rate of 2.5 part by weight by 100 parts $CH_2$ equivalent in the feedstock methanol provides a product yield that is substantially the same, as shown in Table 1. These continuous runs are conducted at the same conditions.

TABLE I

| | Hydrocarbon Product Yield, Wt % | |
|---|---|---|
| Component | Without Recycle | With ethene Recycle |
| $C_1$ | 0.8 | 0.8 |
| $C_2$ | 0.3 | 0.3 |
| $C_2=$ | 2.5 | 2.7 |
| $C_3$ | 4.4 | 4.5 |
| $C_3=$ | 4.6 | 4.5 |
| $nC_4$ | 2.1 | 2.1 |
| $iC_4$ | 10.8 | 10.4 |
| $C_4=$ | 5.4 | 5.1 |
| $C_5+$ (Gasoline) | 69.1 | 69.6 |
| Total | 100.0 | 100.0 |

T = 407° C.
P = 400kPa,
WHSV = 2.65⁻ (based on HZSM-5 catalyst)

In a typical fixed-bed MTG process, large amounts of isobutane are produced (8 wt% of hydrocarbon). However, there is generally not sufficient $C_3/C_4$ olefins produced (0.4 wt % of hydrocarbons) to consume the isobutane by acid alkylation.

The present invention provides an MTO/Alkylation Plant in parallel with a fixed-bed MTG plant, where the MTO reactor is sized to produce sufficient $C_3/C_4$ olefins react with the excess MTG isobutane, thus maximizing $C_5+$ liquid yield.

In addition to producing $C_3=/C_4=$ olefin alkylate, the plant can be operated to produce $C_5=/i-C_5$ alkylate for use as jet fuel. For a gas based synthetic fuels complex, gas field isobutane or butane isomerization can generate isobutane for feed.

Overall the production of MTO gasoline plus alkylate will increase blended gasoline pool octane because of their high component octanes. Also, by reacting the isobutane out of the $C_4$ plant product, a relatively pure normal butane stream is produced for gasoline pressurization. This will increase gasoline yield since normal butane has a lower vapor pressure than isobutane. Also, the $C_1-C_2$ off gas from MTO can be routed to the Fixed-Bed MTG unit to react $C_2=$ to gasoline. This will eliminate the need for cryogenic separation required to separate ethylene for recycle to the MTO unit.

The alkylation process employed herein is a well known industrial technique for reacting alkenes with tertiary alkanes (isoparaffins), such as isobutane, isopentane, isohexane, etc. The resulting product is a $C_7+$ branched chain paraffinic material useful as aviation gasoline, jet fuel or the like. The alkylation of paraffins can be carried out either thermally or catalytically; however, acid catalyst is preferred. Thermal or noncatalytic alkylation of a paraffin with an olefin is carried out at high temperatures (about 500° C.) and pressures 21-41 MPa (3000-6000 psi). Under these conditions, both normal and isoparaffins can be brought into reaction by a free-radical mechanism. Thermal alkylation is not known to be practiced commercially.

The catalytic alkylation of paraffins involves the addition of an isoparaffin containing a tertiary hydrogen to an olefin. The process is used in the petroleum industry to prepare highly branched paraffins mainly in the $C_7$ to $C_9$ range, that are high-quality fuels. The overall process is complex, requiring control of operating conditions and of catalyst. The process conditions and the product composition depend on the particular acid catalysts involved.

The preferred processes are those brought about by the conventional protonic and Lewis catalysts. Propene can be brought into reaction with an isoparaffin in the presence of either concentrated sulfuric acid or hydrogen fluoride. The heptanes produced by alkylkation of isobutane with propene are mainly 2,3- and 2,4-dimethylpentane. Propene is alkylated preferrably as a component of a $C_3-C_4$ fraction. HF catalysts for alkylation of isobutane with 1- and 2-butenes give both dimethylhexanes and trimethylpentanes. The product obtained from alkylation of isobutane with isobutylene at low temperature (e.g., −25° C.) with hydrogen fluoride is 2,2-4-trimethylpentane.

During use the acid catalysts may become diluted with byproduct hydrocarbons and as a result decrease in activity. Sulfuric acid concentrations are maintained at about 90%. Hydrogen fluoride concentrations of 80–90% are common, although the optimum concentration depends on the reaction temperature and reactor geometry. Operation below these acid concentrations generally causes incomplete conversion or polymerization. With sulfuric acid, the product quality is improved when temperatures are reduced to the range of 0°–10° C. Cooling requirements are obtained by low temperature flashing of unreacted isobutane. With hydrogen fluoride, the reaction process is less sensitive to temperature, and temperatures of 0°–40° C. can be used. Some form of heat removal is essential because the heat of reaction is approximately $14 \times 10^5$ J/Kg (600 Btu/lb) of butenes converted. Typically the elevated pressure for alkylation by these acid catalyst is about 1500 to 3000 kPa (200–300 psig).

In order to prevent polymerization of the olefin as charged, an excess of isobutane is present in the reaction zone. Isobutane-to-olefin molar ratios of 6:1 to 14:1 are common, more effective suppression of side reactions being produced by the higher ratios.

The typical alkylation reaction employs a two-phase system with a low solubility of the isobutane in the catalyst phase. In order to ensure intimate contact of reactants and catalyst, efficient mixing is provided. This is important with sulfuric acid because of the low solubility of isobutane in the catalyst phase. In addition, the higher viscosity of the sulfuric acid requires a greater mixing energy to assure good contact. The solubility of the hydrocarbon reactants in the catalyst phase is increased by the presence of the unsaturated organic diluent held by the acid catalyst. This organic diluent also has been considered a source of carbonium ions that promote the alkylation reaction.

For the hydrofluoric acid system, reactive $i—C_4H_8$ readily alkylates to give an excellent product. The alkylation of pure $1—C_4—H_8$ by itself proceeds with considerable isomerization of the $1—C_4H_8$ to $2—C_4—H_8$ followed by alkylation to give a highly branced product. The presence of i—$C_4H_8$ acceleration reaction and allows less time for olefin isomerization. Consequently, the reaction produces an alkylate with a lowered antiknock value. For the sulfuric acid system, isobutane tends to oligomerize and causes other side reaction products of inferior quality; but the isomerization of 1—$C_4$—$H_8$ to 2—$C_4$—$H_8$ proceeds more completely, thereby favoring formation of superior products. Thus for mixed olefin feeds such as described above, the two factors with both catalyst systems counteract each other to provide products of similar antiknock properties.

The olefin-producing MTO process will simultaneously generate isobutane, but the amount may be insufficient to alkylate the coproduced olefins. A suitable outside source of isobutane is natural gas or a by-product of methanol-to-gasoline (MTG) processes.

Suitable alkylation processes are described in U.S. Pat. Nos. 3,879,489 (Yurchak et al), 4,115,471 (Kesler), 4,377,721 (Chester) and in the Kirk-Othmer Encyclopedia of Chemical Technology, Vol. 2, pp. 50–58 (3rd Ed., 1978) John Wiley & Sons, incorporated herein by reference.

The combined processes are an effective means for converting oxygenated organic compounds, such as methanol, DME, lower aliphatic ketones, aldehydes, esters, etc. to valuable hydrocarbon products. Thermal integration is achieved by employing heat exchangers between various process streams, towers, absorbers, etc.

Various modifications can be made to the system, especially in the choice of equipment and non-critical processing steps. While the invention has been described by specific examples, there is no intent to limit the inventive concept as set forth in the following claims.

I claim:

1. A process for converting oxygenate feedstock to liquid hydrocarbons comprising:
   converting oxygenate feedstock predominantly to gasoline range hydrocarbons in a first reactor zone, in contact with ZSM-5 zeolite catalyst thereby producing a minor amount of excess isobutane;
   separating isobutane from the first reactor effluent;
   converting oxygenate feedstock predominantly to $C_2$-$C_5$ lower olefins in a second reactor zone in contact with zeolite catalyst, while maintaining sufficient production of $C_3$+ olefins in the second reactor zone to react with excess isobutane produced in the first reactor zone;
   separating an ethane rich stream from the second reactor olefinic effluent and further converting the ethene to heavier hydrocarbons in the first reactor zone; and
   alkylating the isobutane with $C_3$+ olefins in a third reactor zone in contact with an acid catalyst.

2. The process of claim 1 wherein feedstock to the first and second reactor zones consists essentially of methanol, dimethylether or mixture thereof and wherein catalyst in said first and second zones comprises acid ZSM-5.

3. The process of claim 2 wherein the first reactor comprises a fixed bed of catalyst wherein isobutane is produced in the amount of about 5 to 10 weight percent of hydrocarbons therein.

4. The process of claim 2 wherein said second reactor zone produces at least 30 weight percent $C_3$-$C_4$ olefins in hydrocarbons therein.

5. A process for producing a high octane gasoline comprising the steps of:
   (a) introducing methanol feedstock into a first catalytic reaction zone to produce gasoline range hydrocarbons and an isobutane stream;
   (b) separating the isobutane stream from the effluent of the first reaction zone;
   (c) introducing methanol feedstock into a second catalytic reaction zone to produce a $C_3$-$C_4$ olefin stream and an ethylene-containing vapor fraction;
   (d) separating the ethylene-containing fraction from the effluent of the second reaction zone;
   (e) separating the $C_3$-$C_4$ olefin stream from the effluent of the second reaction zone; and
   (f) introducing the isobutane stream and a sufficient amount of $C_3$-$C_4$ olefin stream obtained in said second reaction zone to react with the isobutane stream into a third catalytic reaction zone to produce gasoline range hydrocarbons.

6. A process according to claim 5 further comprising recycling the ethylene-containing vapor phase from the second reaction zone to the first reaction zone.

7. A process according to claim 5 wherein the catalyst in said first reaction zone is a zeolite material.

8. A process according to claim 7 wherein the zeolite material is selected from the class consisting of ZSM-5, ZSM-11, ZSM-12, ZSM-22, ZSM-23, ZSM-35 and ZSM-38.

9. A process for converting methanol or dimethylether oxygenate feedstock to liquid hydrocarbons comprising:
   converting a first portion of the feedstock predominantly to gasoline range hydrocarbons a first reaction zone in contact with a fixed bed of acid medium pore zeolite catalyst having an acid cracking activity up to 200, and producing a minor amount of $C_4$+ isoparaffin;
   separating isoparaffin from the first reactor effluent;
   converting a second portion of the feedstock to $C_2$-$C_4$ lower olefins in contact with zeolite catalyst having an acid cracking activity of about 1-50;
   separating an ethene rich stream from the $C_2$-$C_4$ olefins and further converting the ethene to heavier hydrocarbons with the first feedstock portion in contact with said fixed bed of zeolite catalyst; and
   alkylating the isoparaffin with $C_3$-$C_4$ olefins in a liquid reaction zone in contact with an acid alkylation catalyst.

10. The process of claim 9 wherein hydrocarbons produced in the fixed catalyst bed contain not more than 0.4 wt.% of $C_3/C_4$ olefin.

* * * * *